United States Patent
Vitale et al.

(10) Patent No.: US 6,562,325 B2
(45) Date of Patent: *May 13, 2003

(54) USE OF STABILIZED STARCHES IN LOW VOC, POLYACRYLIC ACID-CONTAINING HAIR COSMETIC COMPOSITIONS

(75) Inventors: Melissa J. Vitale, Plainsboro, NJ (US); Maria Tolchinsky, Monmouth Junction, NJ (US); Gary T. Martino, Jamesburg, NJ (US); Daniel B. Solarek, Belle Mead, NJ (US); Ian W. Cottrell, Princeton, NJ (US)

(73) Assignee: National Starch and Chemical Investment Holding Corporation, New Castle, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 81 days.

(21) Appl. No.: 09/277,784

(22) Filed: Mar. 29, 1999

(65) Prior Publication Data

US 2001/0018046 A1 Aug. 30, 2001

Related U.S. Application Data

(63) Continuation-in-part of application No. 09/057,826, filed on Apr. 9, 1998.

(51) Int. Cl.$^7$ .................................................. A61K 7/06
(52) U.S. Cl. .................................. 424/70.15; 424/70.16
(58) Field of Search .......................... 424/70.11, 70.13, 424/70.15, 70.16, 45, 47, DIG. 1, DIG. 2

(56) References Cited

U.S. PATENT DOCUMENTS

| | | | |
|---|---|---|---|
| 3,186,911 A | 6/1965 | Rieger et al. | 167/87.1 |
| 3,479,427 A | 11/1969 | Lieberman et al. | 424/47 |
| 3,507,290 A | 4/1970 | Halleck | 132/7 |
| 3,697,644 A | 10/1972 | Laiderman | 424/70 |
| 3,715,428 A | 2/1973 | Quasius et al. | 424/47 |
| 3,790,664 A | 2/1974 | Krochock et al. | 424/47 |
| 4,059,458 A | 11/1977 | Germino et al. | 106/213 |
| 4,283,384 A | 8/1981 | Jacquet et al. | 424/47 |
| 4,328,319 A | 5/1982 | Osipow et al. | 521/78 |
| 4,364,837 A | 12/1982 | Pader | 252/173 |
| 4,411,891 A | 10/1983 | Mizutani et al. | 424/180 |
| 4,638,822 A | 1/1987 | Grollier et al. | 132/7 |
| 4,663,159 A | 5/1987 | Brode et al. | 424/70 |
| 4,734,478 A | 3/1988 | Tsubakimoto et al. | 527/300 |
| 4,913,743 A | 4/1990 | Brode et al. | 106/162 |
| 5,030,443 A | 7/1991 | Varco et al. | 424/47 |
| 5,124,446 A | 6/1992 | Gruning et al. | 536/120 |
| 5,449,763 A | 9/1995 | Wulff et al. | 536/18.6 |
| 5,482,704 A | 1/1996 | Sweger et al. | 424/70.13 |
| 5,871,756 A * | 2/1999 | Jeffcoat et al. | |
| 6,344,183 B2 * | 2/2002 | Paul et al. | 424/47 |
| 6,413,505 B1 * | 7/2002 | Vitale et al. | 424/70.11 |

FOREIGN PATENT DOCUMENTS

| | | | |
|---|---|---|---|
| EP | 0 149 249 | 7/1985 | C08B/11/145 |
| EP | 0 487 000 | 5/1992 | A61K/7/48 |
| EP | 0 577 519 | 1/1994 | A61K/7/06 |
| EP | 0 797 979 | 10/1997 | A61K/7/06 |
| GB | 1285547 | 8/1972 | C08B/19/04 |
| JP | 54-011108 | 1/1979 | C11D/3/37 |
| JP | 55-45602 | 3/1980 | A61K/7/00 |
| JP | 61210008 A | 9/1986 | A61K/7/00 |
| WO | 98/01109 | 1/1998 | A61K/7/48 |

* cited by examiner

Primary Examiner—Jose' G. Dees
(74) Attorney, Agent, or Firm—Karen G. Kaiser

(57) ABSTRACT

The present invention is directed to a low VOC, non-aerosol, polyacrylic acid containing hair cosmetic compositions which contain stabilized starches, particularly those derivatized by alkylene oxides, about 01.–0.0% polyacrylic acid, up to about 15% solvent, and water. The derivatized starch may be hydrolyzed, particularly enzymatically hydrolyzed by at least one endo-enzyme. In addition, the starch may be cationically modified with a low degree of substitution. Use of such starches is novel and advantageous in that they are compatible with polyacrylic acid, providing a clear, solution with a stable viscosity. Further, the resultant composition provides a clear film which is not tacky, good stiffness, and improved humidity resistance.

29 Claims, No Drawings

USE OF STABILIZED STARCHES IN LOW VOC, POLYACRYLIC ACID-CONTAINING HAIR COSMETIC COMPOSITIONS

This application is a continuation-in-part of U.S. Ser. No. 09/057,826 filed Apr. 9, 1998.

BACKGROUND OF THE INVENTION

The present invention relates to novel non-aerosal, low VOC polyacrylic acid-containing hair cosmetic compositions, particularly hair fixative compositions, which contain nonionically derivatized starches and to a process for setting hair utilizing such compositions.

In their most basic form, hair cosmetic compositions contain a film-forming polymer, which acts as the cosmetic, and a delivery system, which is usually one or more alcohols, a mixture of alcohol and water, or water.

The hair setting or styling process ordinarily involves the application of an aqueous solution or dispersion of one or more film-forming materials to combed hair which has previously been wetted or dampened whereupon the treated hair is wound on curlers or otherwise styled and dried. In the alternative, application of this solution or dispersion may be to hair which has already been styled and dried. Once the aqueous solution or dispersion has dried, the individual hairs will have a film deposited thereon which presence will prolong the retention of curls or other desired configurations in the user's hair. Furthermore, the presence of such films will impart such desirable properties as body and smoothness.

To be effective, the film-forming ingredients of a hair cosmetic composition preferably meet a number of requirements. The film derived from these ingredients should be flexible, yet possess strength and elasticity. The ingredients should display good adhesion to hair so as to avoid dusting or flaking off with the passage of time or when the hair is subjected to stress; should not interfere with the combing and brushing of the hair; should remain free of tack or gumminess under humid conditions; should be clear, transparent, and glossy, and should maintain clarity upon aging. Further, the ingredients should maintain good antistatic properties and should be easily removable by washing with water and either a soap or shampoo.

Many film-forming agents have been used in hair cosmetic compositions including, for example, a colloidal solution containing a gum such as tragacanth or a resin such as shellac. The films formed of these materials are, however, quite brittle and the form holding the setting is easily broken if the hair is disturbed. This not only reduces the hair holding power of the material, but also leads to undesirable flaking. Further, some of these film-formers, particularly the resins, are water insoluble and therefore not easily removed with water and soap or shampoo.

Starches are often preferred over resins as they are more cost effective and natural. Hair cosmetic compositions which contain starches are also known in the art. For example, GB 1,285,547 discloses a hair setting composition containing a highly substituted cationic starch having an amylose content of more than 50% by weight. EP 487 000 discloses cosmetic compositions which contain enzymatically degraded, optionally crosslinked starches. However, such derivatives are not significantly soluble in water.

Due to environmental regulations controlling the emission of volatile organic compounds (VOCs) into the atmosphere, VOC emissions have been restricted to 80% in some states, and will soon be restricted to 55% in California. VOC is measured as a wt/wt % based upon the hair cosmetic formulation. As used herein, a volatile organic compound containing from 1 to 10 carbon atoms, which has a vapor pressure of at least 0.1 mm Hg at 20° C., and is photochemically active. Water is generally substituted for at least a portion of the volatile organic compounds and so has become a greater component in hair cosmetic compositions.

Water is generally substituted for at least a portion of the volatile organic compounds and so has become a greater component in hair cosmetic compositions. Such aqueous-based compositions not only meet the low VOC regulations, but are also environmentally friendly and generally lower in cost.

Most starches are incompatible with water in that they are not fully soluble or dispersible, resulting in starch precipitates. Further, most starches are incompatible with the thickener polyacrylic acid, causing the hair cosmetic to lose its viscosity. Surprisingly, it has now been discovered that nonionically derivatized starches are useful in low VOC, polyacrylic acid containing hair cosmetic compositions in that they provide a clear solution with a stable viscosity, good fixative properties, and improved humidity resistance.

SUMMARY OF THE INVENTION

The present invention is directed to a non-aerosol, polyacrylic acid containing, low VOC hair cosmetic compositions which contain nonionically derivatized starches, particularly those derivatized by alkylene oxides. The starch may be hydrolyzed, particularly enzymatically hydrolyzed by at least one endo-enzyme. In addition, the derivatized, hydrolyzed starch may be modified, particularly cationically with a low degree of substitution. Use of such starches is novel and advantageous in that they are compatible with polyacrylic acid, providing a clear solution with a stable viscosity. Further, the resultant composition provides a clear film which is not tacky, good stiffness, improved humidity resistance, and substantive to hair and skin.

The present hair cosmetic composition contains a hair fixative effective amount of the starch, particularly from about 0.5 to about 15% by weight, up to about 15% of a solvent, 0.1–1.0% polyacrylic acid by weight, a neutralizer in an amount necessary to neutralize the polyacrylic acid and sufficient water to bring the composition up to 100%.

An object of this invention is to provide a novel low VOC polyacrylic acid containing hair cosmetic composition which contains nonionically derivatized starches.

Another object of this invention is to provide a novel hair cosmetic composition which contains polyacrylic acid and nonionically derivatized starches which have been hydrolyzed.

Still another object of this invention is to provide a novel hair cosmetic composition which contains polyacrylic acid and starches which have been derivatized with propylene oxide and enzymatically hydrolyzed.

Yet another object of this invention is to provide a novel hair cosmetic composition which contains polyacrylic acid and starches which have been nonionically derivatized, hydrolyzed, and cationically modified to a low DS.

A further object of this invention is to provide a novel hair cosmetic composition which contains polyacrylic acid and starches which have been derivatized with propylene oxide, enzymatically hydrolyzed and modified with 3-chloro-2-hydroxypropyltrimethly ammonium chloride.

A still further object of this invention is to provide a novel low VOC, polyacrylic acid containing hair cosmetic composition which includes starch and has improved humidity resistance, and superior stability.

These and other objects of the present invention will become apparent to one skilled in the art from the following detailed description and examples below.

DETAILED DESCRIPTION OF THE INVENTION

The present invention is directed to a low VOC, non-aerosol, polyacrylic acid containing hair cosmetic compositions which contain nonionically derivatized starches, particularly those derivatized by alkylene oxides. The derivatized starch may be hydrolyzed, particularly enzymatically hydrolyzed by at least one endo-enzyme. In addition, the derivatized starch may be cationically modified with a low degree of substitution (DS). The degree of substitution, as used herein, is intended to describe the number of ester substituted groups per anhydroglucose unit of the starch molecule. Use of such starches is novel and advantageous in that they are compatible with polyacrylic acid, providing a clear, low VOC solution with a stable viscosity. Further, the resultant composition provides a clear film which is not tacky, good stiffness, and improved humidity resistance.

The present hair cosmetic composition contains a hair fixative effective amount of the starch, particularly from about 0.5 to about 15% by weight, more particularly from about 2 to about 10%; less than about 15% solvent, 0.1–0.1% polyacrylic acid, and sufficient water to bring the composition to 100%.

All starches and flours (hereinafter "starch") are suitable for use herein and may be derived from any native source. A native starch or flour as used herein, is one as it is found in nature. Also suitable are starches and flours derived from a plant obtained by standard breeding techniques including crossbreeding, translocation, inversion, transformation or any other method of gene or chromosome engineering to include variations thereof. In addition, starch or flours derived from a plant grown from artificial mutations and variations of the above generic composition which may be produced by known standard methods of mutation breeding are also suitable herein.

Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 45% by weight amylose. Particularly suitable in the present inventions are amylose containing starches, more particularly high amylose starches, most particularly high amylose corn starches.

The starch is first nonionically derivatized using an ester or ether which is compatible with the system, particularly with the solvent. Methods of derivatization are well known in the art and may be found for example in *Starch Chemistry and Technology*, 2nd ed., Edited by Whistler, et al., Academic Press, Inc., Orlando (1984) or *Modified Starches: Properties and Uses*, Wurzburg, O. B., CRC Press, Inc., Florida, (1986).

Nonionic reagents include, but are not limited to alkylene oxides such as ethylene oxide, propylene oxide, and butylene oxide, acetic anhydride, and butyl ketene dimer. Particularly suitable nonionic reagents are the alkylene oxides, more particularly propylene oxide. The nonionic reagent is added in an amount of from about 1 to 50%, particularly from about 5 to 25%, more particularly from about 7.5 to 18%.

For example, the starch may be derivatized using propylene oxide as follows. An aqueous starch slurry containing from about 5 to about 40%, particularly 30 to 40%, solids is prepared. From about 20 to about 30% percent sodium sulfate based on the weight of the starch is added. The pH is then adjusted to about 11 to about 13 by addition of a 3% sodium hydroxide solution in an amount of from about 40 to about 60% based upon the weight of the starch. The desired amount of propylene oxide is added. The temperature is brought to the range of about 35 to 50° C., particularly about 40° C., and the process is allowed to continue for about 18 to about 24 hours.

The starch is generally at least partially gelatinized. If conversion is to be accomplished enzymatically, the gelatinization is conventionally conducted prior to conversion. Gelatinization may be accomplished using any technique known in the art, particularly steam cooking, more particularly jet-cooking, and then converted (hydrolyzed). The conversion is important if a reduced molecular weight starch and a reduced viscosity of the starch solution or dispersion is desired, such as when the starch is to be used in a hair spray. The conversion may be accomplished by any method known in the art, such as by enzymes, acid, dextrinization, man-ox, or oxidation, particularly by enzymes. If conversion is conducted using acid or oxidation methods, then it may be done prior to or after derivatization of the starch.

The enzymatic hydrolysis of the starch base is carried out using techniques known in the art. Any enzyme or combination of enzymes, known to degrade starch may be used, particularly endo-enzymes. Enzymes useful in the present application include, but are not limited to, α-amylase, β-amylase, maltogenase, glucoamylase, pullulanase, particularly α-amylase and pullulanase. The amount of enzyme used is dependent upon the enzyme source and activity, base material used, and the amount of hydrolysis desired. Typically, the enzyme is used in an amount of from about 0.01 to about 1.0%, particularly from about 0.01 to 0.3%, by weight of the starch.

The optimum parameters for enzyme activity will vary depending upon the enzyme used. The rate of enzyme degradation depends upon factors known in the art, including the enzyme type and concentration, substrate concentration, pH, temperature, the presence or absence of inhibitors, and the degree and type of modification. These parameters may be adjusted to optimize the digestion rate of the starch base.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

The optimum parameters for enzyme activity will vary depending upon the enzyme used. The rate of enzyme degradation depends upon factors known in the art, including the enzyme concentration, substrate concentration, pH, temperature, the presence or absence of inhibitors, and the degree and type of modification. These parameters may be adjusted to optimize the digestion rate of the starch base.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

In general, the enzyme reaction will take from about 0.5 to about 24 hours, particularly about 0.5 to about 4 hours. The time of the reaction is dependent upon the type of starch used, the amount of enzyme used, and the reaction parameters of solids percent, pH, and temperature.

The enzyme degradation is then terminated by any technique known in the art such as acid or base deactivation, heat deactivation, ion exchange, and solvent extraction. For example, acid deactivation may be accomplished by adjusting the pH to lower than 2.0 for at least 30 minutes or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The conversion reaction is continued until the starch is sufficiently degraded to provide the desired viscosity, particularly a viscosity of from about 7 to about 80 seconds, more particularly from about 10 to about 60 seconds, measured at 19% w/w solid concentration at room temperature using a standard funnel method. The resultant product may be further characterized by a dextrose equivalent (DE) of from about 2 to about 40 and/or a water fluidity of about 60 to 80.

Funnel viscosity, as used herein, is defined by the following procedure. The starch dispersion to be tested is adjusted to 19% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder in then inverted over the funnel so that the contents draw (flow) into the funnel while the sample is running. Using a timer, the time required for the 100 ml sample to flow through the apex of the funnel is recorded.

The glass portion of the funnel is a standard 580, thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip which is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

Finally, the starch may be cationically treated by well known reagents containing amino, imino, ammonium, sulfonium, or phosphonium groups. Such cationic derivatives include those containing nitrogen containing groups comprising primary, secondary, tertiary and quaternary amines and sulfonium and phosphonium groups attached through either ether or ester linkages. Cationic modification, particularly tertiary amino or quaternary ammonium etherification of starch, typically prepared by treatment with 3-chloro-2-hydroxypropyltrimethly ammonium chloride, 2-diethylaminoethyl chloride, epoxypropyltrimethylammonium chloride, 3-chloro-2-hydroxypropyidimethyl dodecyl ammonium chloride, and 4-chloro-2-butenyltrimethylammonium chloride. Methods of cationically modifying starch are well-known in the art and may be found, for example, in *Starch Chemistry and Technology*, $2^{nd}$ ed., Edited by Whistler, et al., Academic Press, Inc. Orlando (1984) or *Modified Starches: Properties and Uses*. Wurzburg, O. B., CRC Press, Inc., Florida, (1986).

The cationic modification of the starches must be to a low degree of substitution (DS), from about 0.05 to about 1.0, preferably from about 0.1 to about 0.5, most particularly from about 0.1 to 0.3% N.

In general, the degree of nonionic derivatization desired will be greater when the starch is not modified than when the starch is modified.

Optionally, the starch may then be neutralized by raising the pH of the solution to from about 5 to about 9. This may be done by any method known in the art, particularly by the addition of amino methyl propanol, sodium hydroxide, potassium hydroxide, or other bases known in the art.

The starch solution is generally filtered to remove impurities, particularly fragmented starch. Filtration may be by any technique known in the art, particularly by filtration through diatomaceous earth.

The starch may be used as a solution or may be recovered in powdered form by conventional techniques, such as drum-drying or spray-drying.

The modified starch may further be blended or coprocessed with other fixative or conditioning polymers. Such polymer may be selected from polymers known in the art, such as vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/ octylacrylamide, acrylates copolymer, acrylates/ hydroxyacrylates copolymer, and alkyl esters of polyvinylmethylether/maleic anhydride, diglycoll cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/ vinylpyrrolidone/methacryloamidopropyl trimethylammonium chloride terpolymer, methacrylates/acrylates copolymer/amine salt, polyvinylcaprolactam, polyurethanes, polyquaternium-4, polyquaternium-10, polyquaternium-11, polyquaternium-46, hydroxypropyl guar, hydroxypropyl guar hydroxypropyl trimmonium chloride, polyvinyl formamide, polyquaternium-7, and hydroxypropyl trimmonium chloride guar particularly polyvinyl pyrrolidone.

To coprocess the starch and the polymer, the polymer is dissolved in water. The modified starch is then slurried into the dispersed polymer and the slurry is processed. Processing includes cooking and drying, particularly jet cooking and spray drying, and includes the methods disclosed in U.S. Pat. Nos. 5,149,799; 4,280,851; 5,188,674 and 5,571,552 incorporated herein by reference.

A polyacrylic acid, particularly a crosslinked polyacrylic acid, is used to thicken the hair cosmetic composition in an amount of from about 0.1–1.0% by weight of the composition. Polyacrylic acids are known in the art as thickeners for hair cosmetic compositions and are commercially available, for example Carbopol® (commercially available from B. F. Goodrich in Cleveland, Ohio).

Additionally, the system must be neutralized using techniques known in the art such as addition of triethanolamine, 2-amino 2-methyl 1-propanol and other organic amines; or sodium hydroxide and other inorganic neutralizers.

Optional conventional additives may also be incorporated into the hair spray compositions of this invention to provide certain modifying properties to the composition. Included among these additives are plasticizers, such as glycerine, glycol and phthalate esters; emollients, lubricants and penetrants, such as lanolin compounds; fragrances and perfumes; UV absorbers; dyes and other colorants; anticorrosion agents; detackifying agents; combing aids and conditioning agents; antistatic agents; neutralizers; glossifiers; preservatives; emulsifiers; surfactants; viscosity modifiers; gelling agents; opacifiers; stabilizers; sequestering agents; chelating agents; pearling agents; and clarifying agents. Such additives are commonly used in hair cosmetic compositions known heretofore. These additives are present in small, effective amounts to accomplish their function, and generally will comprise from about 0.1 to 10% by weight each, and from about 0.1 to 20% by weight total, based on the weight of the composition.

The instant starch-containing hair care compositions may also be combined with other modified or unmodified starches that provide added functional benefits. For example, formulations with 2-chloroethylamino dipropionic acid derivatives of potato starch or hydroxypropyl starch phosphate may be incorporated for thickening or rheology modification in hair styling lotions and creams, and starches such as tapioca starch, corn starch, or aluminum starch octenyl succinate may be used in the hair care compositions as aesthetic enhancers to provide silkier, smoother formulations. Modified starches, as used herein, is intended to include without limitation, converted starches, cross-linked starches, acetylated and organically esterified starches, hydroxypropylated and hydroxyethylated starches, phosphorylated and inorganically esterified starches, cationically, anionically or zwitterionically modified starches, and succinated and substituted succinated starches. Such modified starches are known in the art for example in *Modified Starches: Properties and Uses* by Wurzburg. Particularly suitable modified starches include hydroxypropylated starches, octenyl succinate derivatives, and 2-chloroethylamino dipropionic acid derivatives.

The delivery system in most cases will be water. However, it is possible to use a small amount, less than about 15% of a solvent. Typically, the solvent will be a lower ($C_{1-4}$) alcohol, particularly methanol, ethanol, propanol, isopropanol, or butanol.

To prepare the non-aerosol hair cosmetic composition, a solution of the starch in the solvent/water or water is prepared. Then any other additives may be added.

Hair cosmetic compositions include, but are not limited to, hair fixative compositions and styling aids, such as gels, spray gels, and lotions.

One advantage of the instant starch-containing hair care compositions is that the starches are substantially soluble in water. This allows a substantially solvent-free composition to be formulated. Solubility is important in that the presence of particulate matter (i.e., undissolved starch) ruins the clarity of the composition and may clog the pump valves or other delivery mechanism, interfering with delivery of the composition.

Another advantage of the instant compositions is that they are of relatively stable viscosity. This ensures that the hair care composition remains thick throughout its shelf-life.

A further advantage of the instant hair cosmetic compositions is that they do not become tacky at high relative humidity (RH), unlike many conventional water-based starch-containing hair cosmetic compositions.

The present starches may also be used in skin, oral, and other hair care applications, such as lotions, creams, sun screens, lip balms, tanning products, oral rinses, antiperspirants, shampoos, and conditioners.

The following examples are presented to further illustrate and explain the present invention and should not be taken as limiting in any regard.

EXAMPLES

All percentages in the examples are calculated on a wt/wt basis.

Example 1

Preparation of Starch Modified with Alkylene Oxide a. A 40% aqueous solution of waxy starch was prepared and 25% sodium sulfate was added. The pH was then adjusted to about 11.5 uses a 3% sodium hydroxide solution. The starch was treated with 7.5% propylene oxide. The pH was then adjusted to 5.5 using dilute sulfuric acid.

b. Example 1a was repeated using a propylene oxide level of 15%.

c. Example 1a was repeated using a propylene oxide level of 3%.

d. Example 1a was repeated using a propylene oxide level of 9%.

e. Example 1d was repeated using a potato starch.

f. Example 1a was repeated using a 50% amylose corn starch.

g. Example 1b was repeated using a 70% amylose corn starch.

h. Example 1b was repeated using a tapioca starch.
i. Example 1a was repeated using 14.4% butylene oxide.
j. Example 1b was repeated using potato starch.
k. Example 1g was repeated using 25% propylene oxide.

Example 2

Preparation of Hydrolyzed Starch Modified with Propylene Oxide a. The slurried starch of Example 1a was adjusted to a pH of 5.5 using sulfuric acid and cooled until fully gelatinized. The starch was then hydrolyzed using α-amylase to a funnel viscosity of about 30 seconds.
b. Example 2a was repeated using a 70% amylose starch.
c. Example 2a was repeated hydrolyzing to a funnel viscosity of 10 seconds.
d. Example 2a was repeated hydrolyzing to a funnel viscosity of 60 seconds.

Example 3

Preparation of Starch Modified with Alkylene Oxide and a Cationic Reagent a. A 40% aqueous slurry of Amioca™ starch was prepared. 25% sodium sulfate was added. The pH was then adjusted to about 11.5 by addition of a 3% sodium hydroxide solution. The starch was then treated with propylene oxide at a level of 7.5%. After reaction, the pH was readjusted to 11.5 using 3% NaOH and treated with 2.5% 3-chloro-2-hydroxypropyltrimethyl ammonium chloride. The slurry was allowed to react for 10 hours while maintaining the pH. The starch was then adjusted to pH 5.5 using dilute hydrochloric acid and washed. The starch was cooked until fully gelatinized, allowed to cool, and filtered through Celite.
b. Example 3a was repeated using 5% 3-chloro-2-hydroxypropyltrimethyl ammonium chloride.
c. A 40% aqueous slurry of Amioca™ starch was prepared. 25% sodium sulfate was added. The pH was then adjusted to about 11.50 by addition of a 3% sodium hydroxide solution. The starch was then treated with propylene oxide a level of 7.5%. After reaction the pH was adjusted to 3.5 using sulfuric acid. The solution was allowed to stir for one hour and the pH was then adjusted to 5.5 with 3% sodium hydroxide. Next the starch was cooked until fully gelatinized and hydrolyzed with alpha-amylase to a funnel viscosity of 30 seconds. The starch cook was cooled to room temperature. Octenyl succinic anhydride was then added at a level of 6% while maintaining the pH at 7.5 using 25% sodium hydroxide solution. The starch was allowed to react until caustic consumption stopped. PH was then adjusted to 5.5 using dilute hydrochloric acid solution. The starch was then filtered through Celite (Celite 512 is a diatomaceous earth commercially available from Celite Corporation).

Example 4

Neutralization of the Starch

The starches of example 3 were neutralized by the addition of 2-amino 2-methyl 1-propanol.

Example 5

Preparation of Hair Gel a) The starches of examples 1–4 were are each made into hair gels using the following formula and method.

| Ingredient | Amount (% w/w) |
|---|---|
| Starch | 3.0 |
| Carbopol[a] | 0.6 |
| TEA[b] | 0.6 |
| Water | 95.8 |

[a]Carbopol is a polyacrylic acid commercially available from B.F. Goodrich in Cleveland, Ohio.
[b]TEA is triethanolamine The starch is dissolved in 50 g water and the TEA is mixed in until homogenous. The polyacrylic acid is mixed into the remaining water to form a solution. The starch mixture is then slowly added to the polyacrylic acid solution with continuous stirring.

Example 6

Performance of Instant Starches in a Model Hair Gel

The hair gels of example 5 were tested for clarity, viscosity, and stability. A control was made using unmodified waxy corn starch. Clarity was rated on a scale of 1 to 5: 1=clear, 2=slightly hazy, 3=hazy, 4=very turbid, and 5=opaque. Viscosity was measured using a Brookfield viscometer. Stability was determined by whether the gel thickened to the proper viscosity. The results are shown in Table I, below.

| Starch | Clarity | Viscosity | Stability |
|---|---|---|---|
| Control | 4.5 | 70,000–90,000 cps | Yes |
| Example 3c | 4 | <70,000 cps | No |
| Example 1a | 4 | 70,000–90,000 cps | Yes |
| Example 1b | 3 | 70,000–90,000 cps | Yes |
| Example 3b | 4 | 70,000–90,000 cps | Yes |
| Example 3a | 3 | 70,000–90,000 cps | Yes |
| Example 1i. | 4 | 70,000–90,000 cps | Yes |
| Example 1e | 4 | 70,000–90,000 cps | Yes |
| Example 1g | 3 | 70,000–90,000 cps | Yes |
| Example 1k | 2 | 70,000–90,000 cps | Yes |

Example 7

Preparation of All-Natural Texturizing Fixative Lotion

|  | Ingredients | % By Weight |
|---|---|---|
|  | Phase A: |  |
|  | Deionized Water | 55.85 |
| (1) | potato starch modified | 1.75 |
| (2) | Brij 78 | 2.00 |
|  | Phase B: |  |
| (3) | DC 345 | 7.50 |
| (4) | DC 200 | 2.50 |
|  | Phase C: |  |
| (5) | Lanette O | 1.40 |
| (6) | Germall II | 1.00 |
|  | Phase D: |  |
|  | Propylene Glycol | 5.00 |
|  | Example 1g | 3.00 |
|  | Phase E: |  |
|  | Deionized Water | 20.00 |
|  |  | 100.00 |

INCI Designations:
 (1) Potato Starch Modified (National Starch and Chemical)
 (2) Steareth-20 (ICI Surfactants)
 (3) Cyclomethicone (Dow Corning)
 (4) Dimethicone (Dow Corning)
 (5) Cetearyl Alcohol (Henkel)
 (6) Diazolidinyl Urea (Sutton Labs)

Procedure:

Potato starch modified was added to cold water and mixed for 2 minutes. Starch solution was heated to 80° C. whilst mixing at moderate speed. Mixing was continued for 25 minutes at 80° C. Brij 78 was then added and mixed until dissolved. Phase B was premixed and added to Phase A under high speed (8,000–10,000 RPM). Lanette O was then added at 80° C. and mixed and the Germall II was added. Phase D was premixed and then Phase E was added to Phase D with mixing. Phase DE was added to Phase ABC and mixing was continued for approximately 10–15 minutes.

We claim:

1. A hair cosmetic composition comprising:
 a) a fixative effective amount of a stabilized starch wherein the starch is nonionically derivatized;
 b) from about 0.1 to about 1.0% of a polyacrylic acid by weight of the composition:
 c) up to about 16% solvent; and
 d) water;
 wherein the composition is a non-aerosol, low VOC formulation.

2. The composition of claim 1, wherein the starch is present in an amount of from about 0.5 to 15% by weight of the composition.

3. The composition of claim 1, wherein the starch is present in an amount of about 2 to 10% by weight of the composition.

4. The composition of claim 1, wherein the starch is a high amylose starch.

5. The composition of claim 1, wherein the starch is nonionically derivatized using from about 1 to about 50% of a non ionic modifying agent.

6. The composition of claim 5, wherein the starch is nonionically derivatized using from about 5 to about 25% of a nonionic modifying agent.

7. The composition of claim 1, wherein the starch is nonionically derivatized using a reagent selected from the group consisting of alkylene oxide, acetic anhydride, and butyl ketene dimer.

8. The composition of claim 7, wherein the starch is nonionically derivatized using an alkylene oxide.

9. The composition of claim 8, wherein the starch is nonionically derivatized using propylene oxide.

10. The composition of claim 1, wherein the starch is further at least partially hydrolyzed.

11. The composition of claim 1, wherein the starch is further cationically modified.

12. The composition of claim 11, wherein the starch is cationically modified using a reagent containing a group selected from the group consisting amino, imino, ammonium, sulfonium, and phosphonium.

13. The composition of claim 11, wherein the starch is modified using a reagent selected from the group consisting of 3-chloro-2-hydroxypropyltrimethly ammonium chloride, 2-diethylaminoethyl chloride, epoxypropyltrimethylammonium chloride and 4-chloro-2-butenyltrimethylammonium chloride.

14. The composition of claim 1, further comprising a fixative or conditioning polymer.

15. The composition of claim 14, wherein the fixative or conditioning polymer is selected from the group consisting of vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates copolymer, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer, methacrylates/acrylates copolymer/amine salt, polyvinylcaprolactam, polyurethanes, polyquaternium-4, polyquaternium-10, polyquaternium-11, polyquaternium-46, hydroxypropyl guar, hydroxypropyl guar hydroxypropyl trimmonium chloride, polyvinyl formamide, polyquarternium-7, and hydroxypropyl trimmonium chloride guar.

16. The composition of claim 15, wherein the polymer is polyvinyl pyrrolidone.

17. The composition of claim 15, wherein the starch and polymer are slurried together, cooked, and dried.

18. A hair cosmetic composition comprising:
 a) a fixative effective amount of a propylene oxide modified high amylose starch/polyvinyl pyrrolidone (PVP) mixture prepared by slurrying the modified starch with the PVP, jet cooking, and spray drying;
 b) up to about 15% of a solvent;
 c) from about 0.1 to about 1.0% polyacrylic acid by weight of the composition: and
 (d) water.

19. The composition of claim 1, wherein the composition is substantially solvent-free.

20. The composition of claim 18, wherein the composition is substantially solvent-free.

21. The composition of claim 1, further comprising at least one additional modified or unmodified starch.

22. The composition of claim 21, wherein the additional starch is selected from the group consisting of hydroxypropylated starches, octenyl succinate derivates, and 2-chloroethylamino dipropionic acid derivatives.

23. The composition of claim 18, further comprising of at least one additional modified or unmodified starch.

24. The composition of claim 19, wherein the additional starch is selected from the group consisting of hydroxypropylated starches, octenyl succinate derivates, and 2-chloroethylamino dipropionic acid derivatives.

25. A method of styling hair comprising applying to the hair the composition of claim 1.

26. A method of styling hair comprising applying to the hair the composition of claim 18.

27. A method of styling hair comprising applying to the hair the composition of claim 19.

28. A method of styling hair comprising applying to the hair the composition of claim 20.

29. A hair cosmetic composition comprising:
 a) a fixative effective amount of a mixture of propylene oxide modified high amylose starch and a cellulose polymer selected from the group consisting of chosen from the group consisting of polyquaterlum-4, polyquaterium-7, polyquaterium-10, polyquaterium-11 and polyquaterium-46, wherein the starch and polymer are slurried together, jet cooked and spray dried:

b) up to about 15% of a solvent;

c) from about 0.1 to about 1.0% polyacrylic acid by weight of the composition; and d) water.

* * * * *